US011179192B2

(12) United States Patent
Whayne et al.

(10) Patent No.: US 11,179,192 B2
(45) Date of Patent: Nov. 23, 2021

(54) ABLATION DEVICES AND METHODS OF USE

(71) Applicant: Atricure, Inc., Mason, OH (US)

(72) Inventors: James G. Whayne, Cary, NC (US); Sidney D. Fleischman, Durham, NC (US)

(73) Assignee: AtriCure, Inc., Mason, OH (US)

( * ) Notice: Subject to any disclaimer, the term of this patent is extended or adjusted under 35 U.S.C. 154(b) by 758 days.

(21) Appl. No.: 15/224,346

(22) Filed: Jul. 29, 2016

(65) Prior Publication Data

US 2017/0027636 A1   Feb. 2, 2017

Related U.S. Application Data

(60) Provisional application No. 62/198,585, filed on Jul. 29, 2015.

(51) Int. Cl.
| | |
|---|---|
| *A61B 18/14* | (2006.01) |
| *A61B 18/02* | (2006.01) |
| *A61B 18/08* | (2006.01) |
| *A61N 7/02* | (2006.01) |
| *A61B 18/00* | (2006.01) |

(52) U.S. Cl.
CPC .......... *A61B 18/1482* (2013.01); *A61B 18/02* (2013.01); *A61B 18/082* (2013.01); *A61N 7/02* (2013.01); *A61B 2018/00035* (2013.01); *A61B 2018/00214* (2013.01); *A61B 2018/00291* (2013.01); *A61B 2018/00363* (2013.01); *A61B 2018/00577* (2013.01); *A61B 2018/00642* (2013.01); *A61B 2018/0293* (2013.01)

(58) Field of Classification Search
CPC ... A61B 18/1482; A61B 18/082; A61B 18/02; A61B 2018/00035; A61B 2018/00291; A61B 2018/00279; A61B 2018/1475; A61B 2018/00214; A61B 2018/00363; A61B 2018/00577; A61B 2018/00642; A61B 2018/0293; A61N 7/02
See application file for complete search history.

(56) References Cited

U.S. PATENT DOCUMENTS

| | | | |
|---|---|---|---|
| 5,871,483 A | 2/1999 | Jackson et al. | |
| 6,205,361 B1* | 3/2001 | Kuzma | A61N 1/05 607/116 |
| 2005/0288666 A1* | 12/2005 | Bertolero | A61B 1/12 606/41 |
| 2006/0122680 A1* | 6/2006 | Auth | A61B 18/1492 607/122 |
| 2008/0114354 A1* | 5/2008 | Whayne | A61B 18/148 606/49 |
| 2011/0098694 A1* | 4/2011 | Long | A61B 18/02 606/21 |
| 2013/0018370 A1 | 1/2013 | Whayne et al. | |

* cited by examiner

*Primary Examiner* — Eun Hwa Kim
*Assistant Examiner* — Adam Z Minchella
(74) *Attorney, Agent, or Firm* — Levine Bagade Han LLP

(57) ABSTRACT

Methods and devices described herein facilitate improved treatment of body organs.

13 Claims, 12 Drawing Sheets

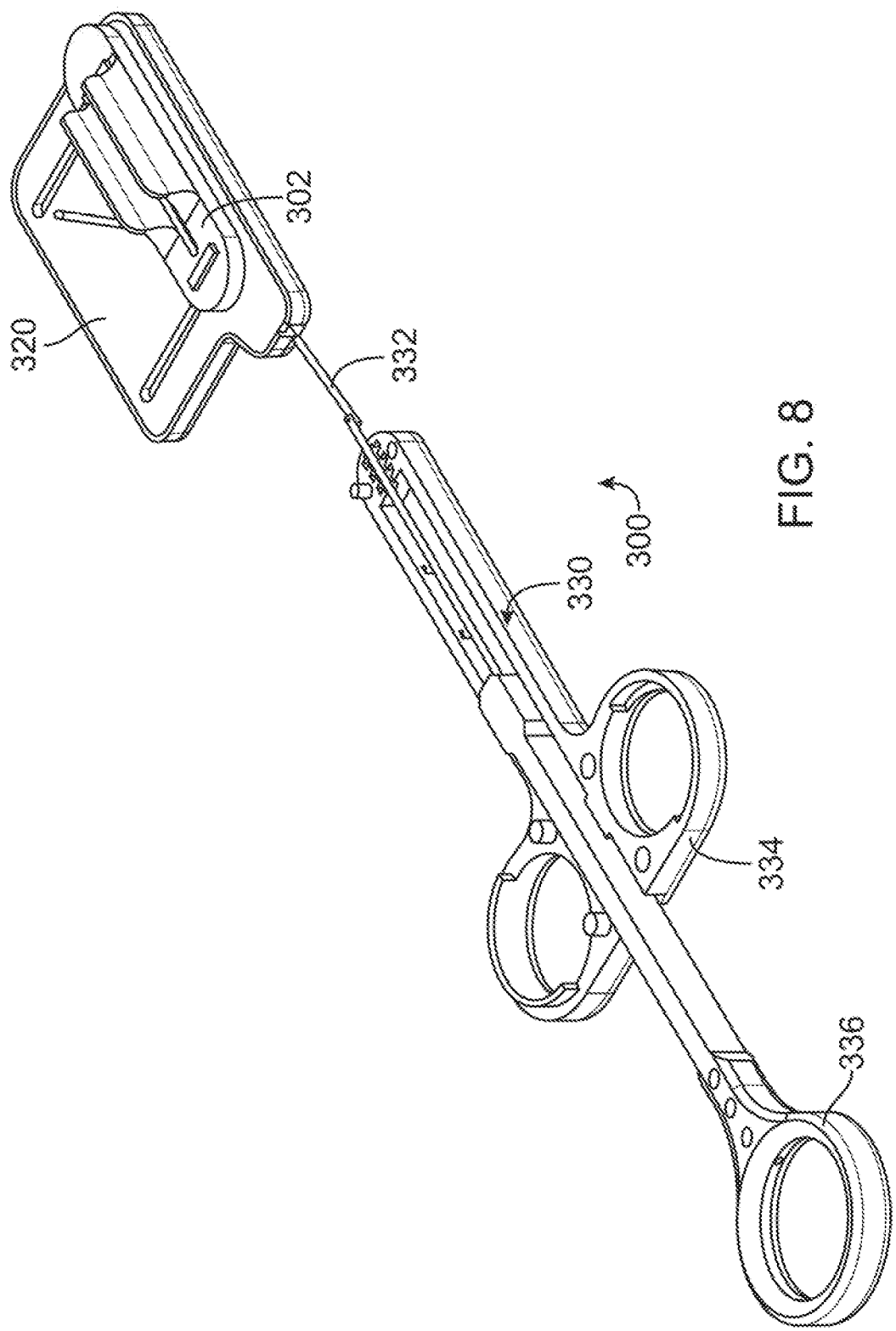

ABLATION DEVICES AND METHODS OF USE

This application is a non-provisional of U.S. Provisional application No. 62/198,585 filed Jul. 29, 2015, entitled "Ablation Devices and Methods of Use". The above filing is hereby incorporated by reference in its entirety.

BACKGROUND OF THE INVENTION

Field of the Inventions

Methods and devices are disclosed herein for therapeutically treating tissue. The devices and methods are suitable for minimally invasive surgery or open surgical procedures. More particularly, methods and devices described herein permit treating large areas of tissue without having to reposition the treatment device. The methods and devices described herein discuss the treatment of cardiac tissue for purposes of illustration. However, the methods and devices can be applied in any application where tissue is treated (e.g., via such modes including heating, cooling, mechanical).

Description of the Related Art

Atrial fibrillation surgery requires creation of an ablation or coagulation lesion in atrial tissue. Typically, a physician creates a lesion using energy (including but not limited to radiofrequency, D.C., microwave, laser or other thermal modalities) to prevent wavelets or electrical signals/impulses that propagate through the atrial tissue to sustain atrial fibrillation or produce atrial flutter, atrial tachycardia, or other arrhythmia.

Many conventional approaches in applying energy to the atrial tissue face difficulties in attempting to create a complete lesion pattern that prevents propagation of the electrical impulse across the lesion pattern. Some factors attributable to these difficulties are tissue contact throughout the length of the electrode(s) is/are not consistent causing variability in the transmission of energy throughout the target length of ablated/coagulated tissue. Moreover, surrounding anatomic features also contributes to the difficulty in creating a complete lesion pattern. As a result, an incomplete lesion or lesion pattern includes one or more gaps of viable of semi-viable tissue that allows propagation of wavelets through tissue and through the lesion pattern.

Another factor in the inability of existing thermal ablation systems to create complete curvilinear, transmural lesions is the presence of convective cooling on the opposite surface of the atrium. This convective cooling produces a heat sink that decreases the maximum temperature at this surface thereby preventing the lesions from consistently extending transmurally through the entire wall of the atrium. This is especially relevant during beating-heart procedures in which the coagulation/ablation probe is placed against the epicardial surface, and blood flowing along the endocardium removes heat thus producing a larger gradient between temperature immediately under the electrodes along the epicardium and that the temperature at the endocardium.

Yet another other deficiency of current approaches is the inability to direct the coagulation of precise regions of soft tissue while avoiding underlying or nearby tissue structures. For example, atrial fibrillation ablation may involve extending a lesion to the annulus near which the circumflex, right coronary artery, and coronary sinus reside; another example involves ablating ventricular tachycardia substrates that reside near coronary arteries or coronary veins. Conventional approaches are unable to selectively ablate desired soft tissue structures and isolate preserved tissue structures from targeted regions.

Traditionally, atrial coagulation patterns were only completed using endocardial coagulation lesions, in such procedures, the physician introduced one or more intravenous catheters through the vasculature to atrial tissue. Endocardial coagulation suffers a drawback in that the physician cannot easily visualize the site being ablated. Furthermore, endocardial coagulation carry a risk of complications due to ablating outward from the endocardial surface including esophageal fistula, thromboembolic complications from coagulum formation, PV stenosis, phrenic nerve palsy and lung damage. Aside from the risks, his difficult to create complete linear lesion lines via an endocardial approach.

Recently, systems have been developed to ablate the cardiac tissue on the epicardium. Epicardial coagulation allows for more comprehensive bi-atrial lesion patterns at the expense of procedural complexity and time. However, many current procedures require significant manipulation of other tissue structures to create the desired lesion pattern. For example, many procedures require one or more ports or trocars placed in a chest wall and/or deflation of a lung to access the target site.

The ability to create lesions is further complicated in those situations where there is a desire to create a treatment pattern (e.g., ablation/coagulation) on a large area of tissue. In such cases, repositioning the device on the surface of tissue can lead to excessive overlap of treated tissue regions as well as increased procedure time. Furthermore, access to the region of tissue might be limited by the surrounding anatomy.

The improved methods and devices described herein offer an improvement to teach a large region of tissue, especially those organs those organs in the thoracic cavity. Variations of these methods and devices address the above described deficiencies for atrial fibrillation and ventricular tachycardia ablation. In addition, the embodiments or variations of the embodiments may address similar deficiencies, which are apparent during other applications involving coagulation of a selected tissue region in a precise manner.

SUMMARY OF THE INVENTION

The devices described herein allow for creation of cardiac lesion patterns on cardiac surfaces. However, the methods and techniques are applicable to non-cardiac treatments as well.

Variations of the devices, methods and procedures described herein include combinations of features of the various embodiments or combination of the embodiments themselves wherever possible.

The present disclosure includes medical devices for treating large areas of tissue surfaces without having to re-position the treatment device. In one example, the medical device includes an elongate shaft comprising at least a plurality of housing shells located at a distal end of the elongate shaft, where the plurality of housing shells each includes a cavity containing an energy transfer element, where each housing shell comprises an opening that exposes the respective energy transfer element; where each of the plurality of housing shells is coupled to at least one adjacent housing shell along a longitudinal edge such that the plurality of housing shells can be folded longitudinally relative to an adjacent housing shell to assume a compact configuration; and the plurality of housing shells comprising at least a first housing shell and a second shell each having a free longitudinal edge such that the plurality of housing shells can be unfolded from the compact configuration to assume a deployment configuration.

In one variation of the medical device, the deployment configuration comprises the energy transfer elements of each of the plurality of housing shells are aligned in parallel to the longitudinal axis of the plurality of housing shells to define a tissue treatment surface having a width greater than a width of the compact configuration.

A variation of the device include a length of the opening along the longitudinal axis of the plurality of housing shells that is greater than a width of the opening. The energy transfer element can span the length of the opening to create a treatment pattern equal to the length of the opening. Moreover, the energy transfer element can also span the width of the opening to create a treatment pattern equal to the width of the opening.

Variations of the device include energy transfer elements that are recessed from the opening within the cavity of the housing shell.

The devices described herein can include one or more vacuum lumens fluidly coupled to the cavity of the housing shell. Additional variations can also include a perfusion lumen fluidly coupled to the cavity.

Variations of the devices can include energy transfer elements selected from the group consisting of an electrically resistive heating element, an RF electrode, a vibrational element, an ultrasonic transducer element, a microwave antenna, and a cryogenic fluid element.

The present disclosure also includes methods for treating tissue. In one example the method includes positioning a cannula adjacent to a region of tissue; advancing a medical device through a distal opening of the cannula, where the medical device includes a plurality of housing shells folded along a longitudinal axis of the plurality of housing shells, where each of the plurality of housing shells comprises an opening that exposes an energy transfer element located within a cavity of each of the housing shells, where a length of each energy transfer element is greater than a width such that the energy transfer element is configured to create an elongate treatment pattern; unfolding the plurality of housing shells such that the openings of each housing shell are oriented in parallel and towards the region of tissue; contacting the plurality of housing shells against a surface of tissue such that each energy transfer element is positioned adjacent to tissue, and applying energy to each energy transfer element to create a plurality of the elongate treatment patterns in the region of tissue.

The method can further include applying a vacuum through at least one cavity of the plurality of housing shells to secure the at least one housing shell against the region of tissue.

The methods described herein can also include applying the vacuum through at least one cavity of the plurality of housing shells to further draw a portion of the region of tissue to contact the energy transfer element. The energy transfer elements can include openings where applying the vacuum through the at least one cavity causes the region of tissue to be pulled into the opening of the at least one energy transfer element.

The methods can further include delivering a fluid through at least one cavity of the plurality of housing shells. In certain variations, the method comprises applying the vacuum through the at least one cavity to cause the tissue region to form a seal against the opening in the at least one of the plurality of housing shells, where the seal causes fluid to flow through the at least one cavity.

BRIEF DESCRIPTION OF DRAWINGS

FIG. 8 shows an example of a positioning system for use with the probe of FIG. 7A.

DETAILED DESCRIPTION

Methods and devices described herein provide for treating regions of tissue with a device that increases coverage of the tissue surface area but can be reduced in diameter for entry or withdrawal at the site through an ordinary access cannula or catheter.

In light of this framework, a number of exemplary variations of the invention are disclosed—mainly in the context of soft tissue coagulation accomplished through less invasive approaches (e.g., thoracoscopic, arthroscopic, laparoscopic, percutaneous, or other minimally invasive procedures). The treatment device variations disclosed herein produce intimate contact specifically between a soft tissue surface and the energy transfer element e.g., an electrode, antenna, or vibration elements used to transmit energy). Such energy modalities can include electrically resistive heat, RF, vibrational/ultrasonic, microwave, cryogenic, electroporation or any other or energy modality used to treat tissue. In those cases where electroporation is used, the energy transfer element can be used to generate the required electricity to open pores of the cell membranes and the fluid source can introduce the biological agent (e.g., the agent containing DNA, chromosomes, etc.)

The integrated vacuum coagulation probe variations may also enable supporting and/or repositioning the soft tissue during coagulation to prevent or minimize shrinking or other change in the shape of the soft tissue associated with heat causing the collagen in the soft tissue to denature. Nevertheless, it should be appreciated that the integrated vacuum coagulation probe devices can be applied to other indications involving devices that are used to coagulate soft tissue where access to the tissue is limited by a small opening into the cavity, confined space at the soft tissue interface, difficult to reach locations, or other anatomic limitation.

An additional potential benefit the subject devices involve the ease of deployment and rapid healing post-procedure. The small incision used to access the soft tissue during such procedures accelerates the healing process and reduces the visible scar. The integrated vacuum coagulation probe devices can be capable of being deployed through a thoracotomy, thoracotomy, median sternotomy, mini-sternotomy, mini-thoracotomy, subxyphoid access, subthoracic access, arthroscopic, or laparoscopic approach, thereby potentially eliminating the need for long incisions to access the soft tissue and corresponding anatomic structures. However, the devices described herein can be used in any type of medical procedure including open surgical procedures.

Figure 1:
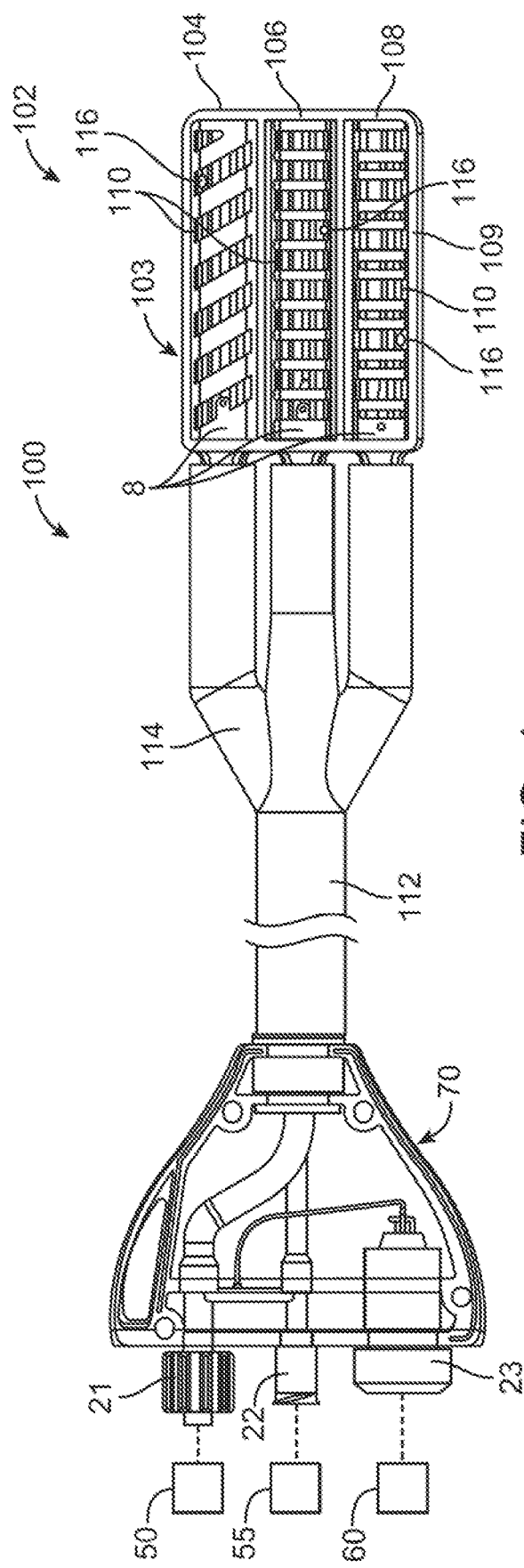
FIG. 1 illustrates an example of a multi-chambered medical device having a number of energy transfer elements that can assume a compact profile.

FIG. 1 illustrates a variation of a medical device 100 that includes a working end 102 towards a distal end of a shaft 112. The working end 102 comprises a plurality of housings or housing shells 103. Each of the plurality of housing shells 104, 106, 108 includes a cavity 110 formed by a wall 109 or lip of the housing shells. The cavity 110 of each housing shell includes an energy transfer element 8 that is exposed in an opening of the housing shell. As discussed below, the energy element 8 can be recessed within the cavity of the respective housing shell such that it is offset from the edge 109 of the wall that defines the perimeter of the opening. In alternate variations, one or more energy transfer elements 8 can be flush with the opening. Moreover. FIG. 1 illustrates each of the housing shells 104, 106, 108 containing energy transfer elements 8 of different configurations. However, any configuration of energy transfer elements 8 can used in the housing shells. In some variations, the energy transfer elements 8 spans the length of the opening to create a treatment pattern equal to the length of the opening. However, alternate variations can include energy transfer elements that are less than a length of the opening. Moreover, one or more housing shells can lack an energy transfer element as discussed below.

FIG. 1 also illustrates the housing shells 104, 106, 108 coupled to an elongate shaft 112. The elongate shaft 112 can comprise a flexible structure or rigid structure depending upon the desired application. Moreover, the elongate shaft 112 can include a manifold 114 that diverts vacuum, fluid, and lines for the power supply to each respective housing shell. Alternatively, the elongate shaft can couple to a single housing shell 103 where the lines for vacuum, fluid, and/or power supply are routed through the housing shell 103 directly adjacent to the elongate shaft 112. In those variation where a manifold is used, the manifold shall allow folding of the housing shells as described below.

In this variation, the device 100 includes a handle 70 having a plurality of connectors 21, 22, 23 for connecting the device 100 to a power supply 60, a fluid source 55 and a vacuum source 50 respectively. Variations of the coagulation device may employ any variety of shapes and sizes for the handles. While the illustrated variation includes a handle 70, variations of the device 100 can include a shaft 112 that removably engages a handle or couples directly a power supply 60, a fluid source 55 and a vacuum source 50.

Most variations of the devices described herein include a connector for a power supply and vacuum source. However, such connectors may be combined in a single connection and locked to the handle. Combining the vacuum and fluid source connectors into a single component interconnected by a bridge designed to provide stability ensures integrity of the connectors while rotating the mating connector into engagement or removing the mating connector. Alternatively, the device may include more connectors than that shown in FIG. 1. In addition, the device 100 can include any number of diagnostic elements 116 positioned within the cavity 110 or on any other portion of the device 100. Such diagnostic elements 116 can include pacing electrodes, temperature sensing electrodes, electrodes intended to measure impedance of the tissue, etc.

Figure 2A:
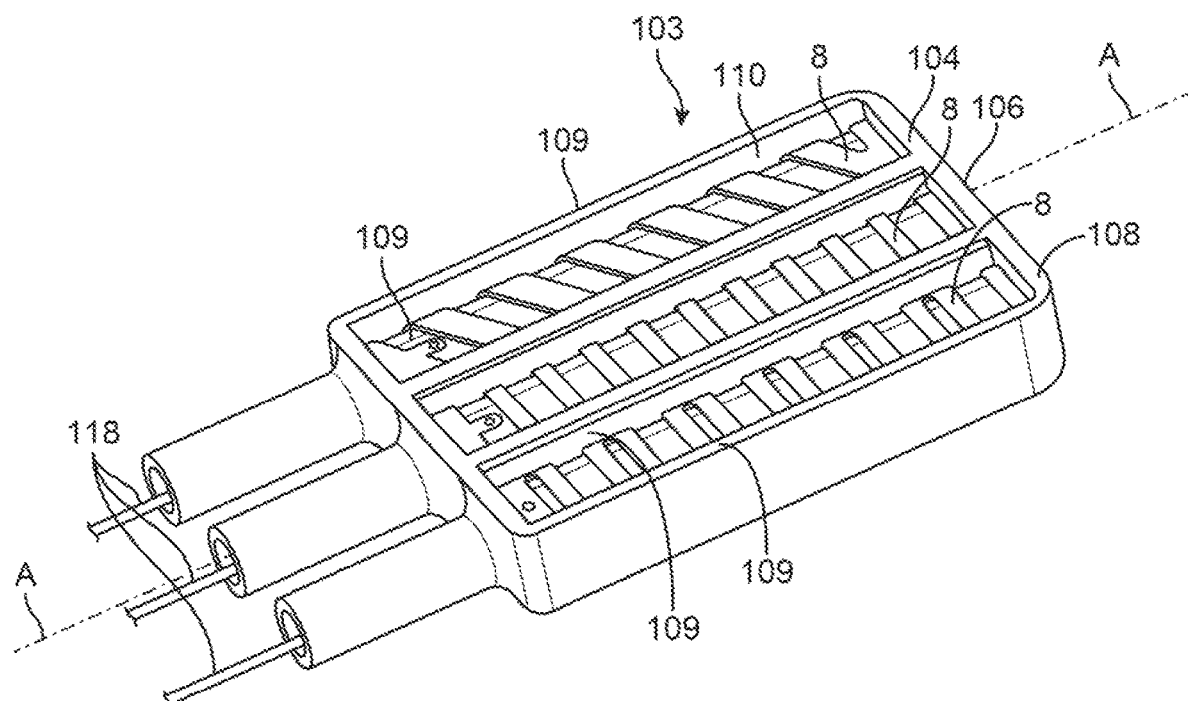
FIGS. 2A to 2C show an isometric view, a side view, and a rear view of the plurality of housing shells of FIG. 1.

FIG. 2A illustrates the plurality of housing shells 103 of FIG. 1. For purposes of illustration, the elongate member 112 and manifold 114 are omitted showing fluid supply lines 118 extending into the cavity 110 of the shells 103. FIG. 2A illustrates each energy transfer element 8 recessed within the cavity 110 of each shell 104, 106, 108 such that the wall 109 of the respective cavity extends beyond the energy transfer element 8. FIG. 2A also illustrates the plurality of housing shells 103 coupled in a manner that allows folding of the housing shells 103 about or along the longitudinal axis A of the housing shells A. In the illustrated variation, each housing shell 104, 106, 108 includes a wall 109 that is coupled to at least one adjacent housing shell along a longitudinal edge (i.e., an edge parallel to the axis A, that borders an adjacent housing shell). Such a configuration allows for the plurality of housing shells to be folded towards each other and rotated about the longitudinal axis A of the plurality of housing shells to assume a compact configuration as shown below. In the illustrated example, center housing shell 106 is coupled to the housing shells 104 and 108 on either side. As shown, the outer housing shells 104 and 108 have a free longitudinal edge that allows the shells 103 to be unfolded.

Figure 2B:
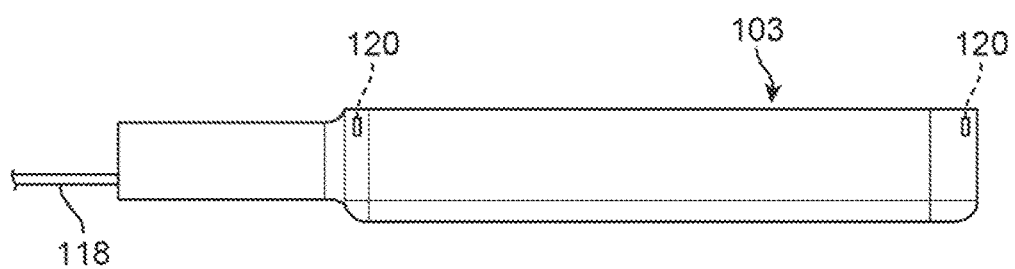
Figure 2C:
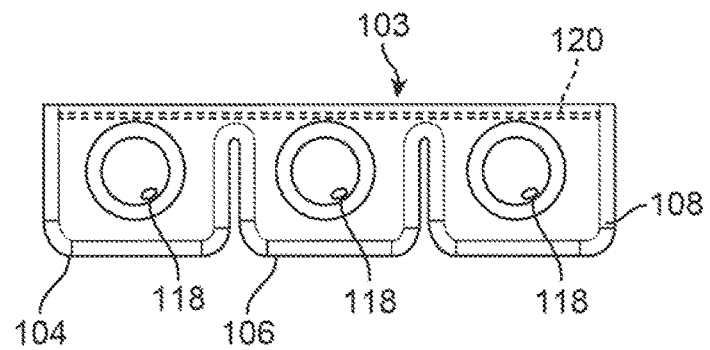

Although not illustrated, the housing shells 103 can include any resilient or reinforcing member 120 that spans in a direction that is transverse to the axis A. Such a reinforcing member 120 can be resilient and allows the housing shells 103 to resume the relatively planar configuration (shown in FIG. 2) after being folded to the compact configuration. FIG. 2B, a side view of the housing, shells 103, and 2C, a rear view of the housing shells 103, illustrate one example of a reinforcing/resilient member 120 located within a portion of the wall 109 of the shells in a direction transverse to the axis A (shown in FIG. 2A.)

The energy transfer elements can comprise a variety of shapes and configurations. For example, the transfer elements can comprise helical windings as described in the commonly assigned patents and applications described below. In those variations of the device using cryoablation, the cryogenic fluid can flow within the energy transfer elements. Alternatively, variations of the device include cryogenic fluid being passed through the housing shell upon generation of a vacuum. In such a variation no energy transfer element is located within the housing unit.

Figure 3A:
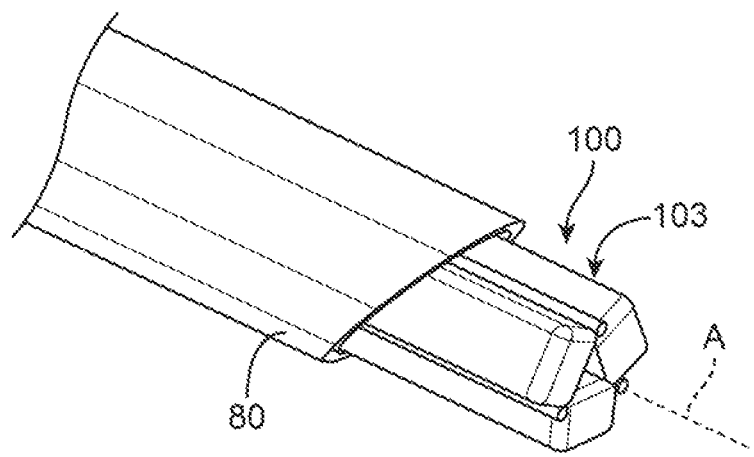
FIG. 3A illustrates a plurality of housing shells each folded about a longitudinal axis such that the plurality of housing shells are folded relative to an adjacent housing shell to assume a compact configuration.

FIG. 3A illustrates the plurality of housing shells 103 each folded about the longitudinal axis A such that the plurality of housing shells 103 are folded longitudinally relative to an adjacent housing shell to assume a compact configuration. As shown, the compact configuration allows for advancement of the medical device 100 through an access cannula

Figure 3B:
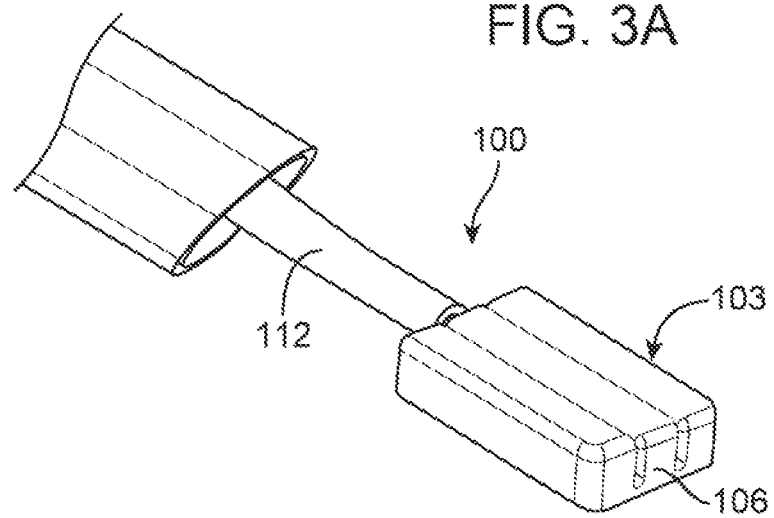
FIG. 3B illustrates a variation of a device where an elongate member couples directly to a single housing shell.
Figure 3C:
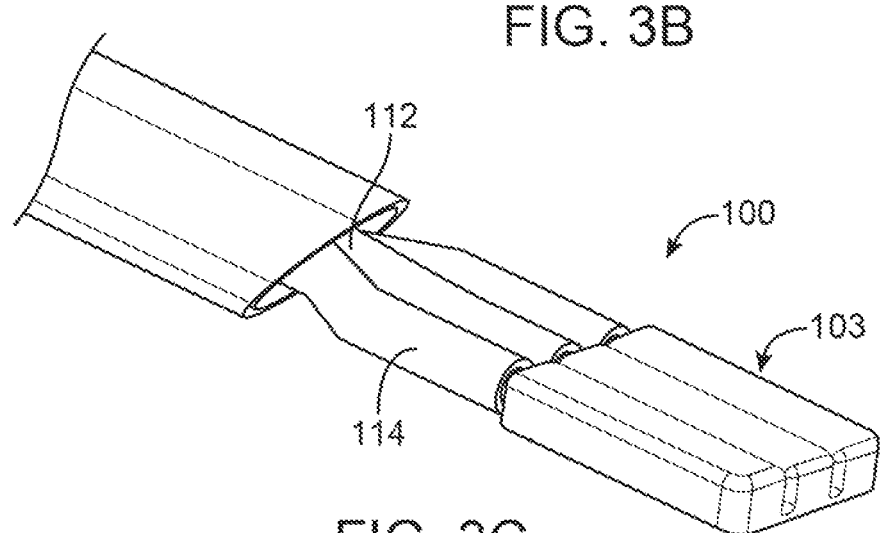
FIG. 3C illustrates a variation of a device where an elongate member couples to the plurality of housing shells using a manifold.

80 or other introducer device. FIGS. 3B and 3C illustrate alternate variations of the medical device 100 after assuming a deployment configuration which results in the housing shells and associated energy transfer elements are aligned in parallel to the longitudinal axis A to define a tissue treatment surface (as measured across the openings of the shells or the total of the energy transfer elements), that has a width greater than a width of the compact configuration.

The devices describe herein can be used with any access device or cannula. For example, the following commonly assigned patents and publications, incorporated by reference herein, discloses examples of such access devices: US20070083082A1 filed on Apr. 21, 2006; US20070083225A1 filed on Apr. 21, 2006; US20110282344A1 filed on May 10, 2011; US20130090532A1 filed on Jun. 7, 2012; U.S. Pat. No. 8,211,011 issued Jul. 3, 2012; U.S. Pat. No. 8,267,951 issued Sep. 18, 2012; US20150112145A1 filed on May 12, 2014; U.S. Pat. No. 8,721,597 issued May 13, 2014; US20150119642A1 filed on Oct. 8, 2014; U.S. Pat. No. 8,858,528 issued Oct. 14, 2014; US20150196316A1 filed on Mar. 25, 2015; U.S. Pat. No. 8,992,557 issued Mar. 31, 2015; and U.S. Pat. No. 8,998,900 issued Apr. 7, 2015.

FIG. 3B illustrates a variation of the device 100 where the elongate member 112 couples directly to the center housing shell 106 alone. Alternatively, the elongate member 112 can couple to any housing shell. For example, the elongate member 112 can couple to the housing shell on either end of the plurality of housing shells. FIG. 3C illustrates the elongate member 112 having a manifold 114 that couples to the housing shells 103 where the parts of the manifold separate and flatten along with the housing shells when in the deployment configuration. Movement towards the deployment configuration can be passive (i.e., such that the housing shells naturally return to the deployment configuration when not restrained). Alternatively, causing movement of the housing shells towards the deployment configuration can require activation (e.g. via a shape memory element, pull wires, etc.)

Figure 4A:
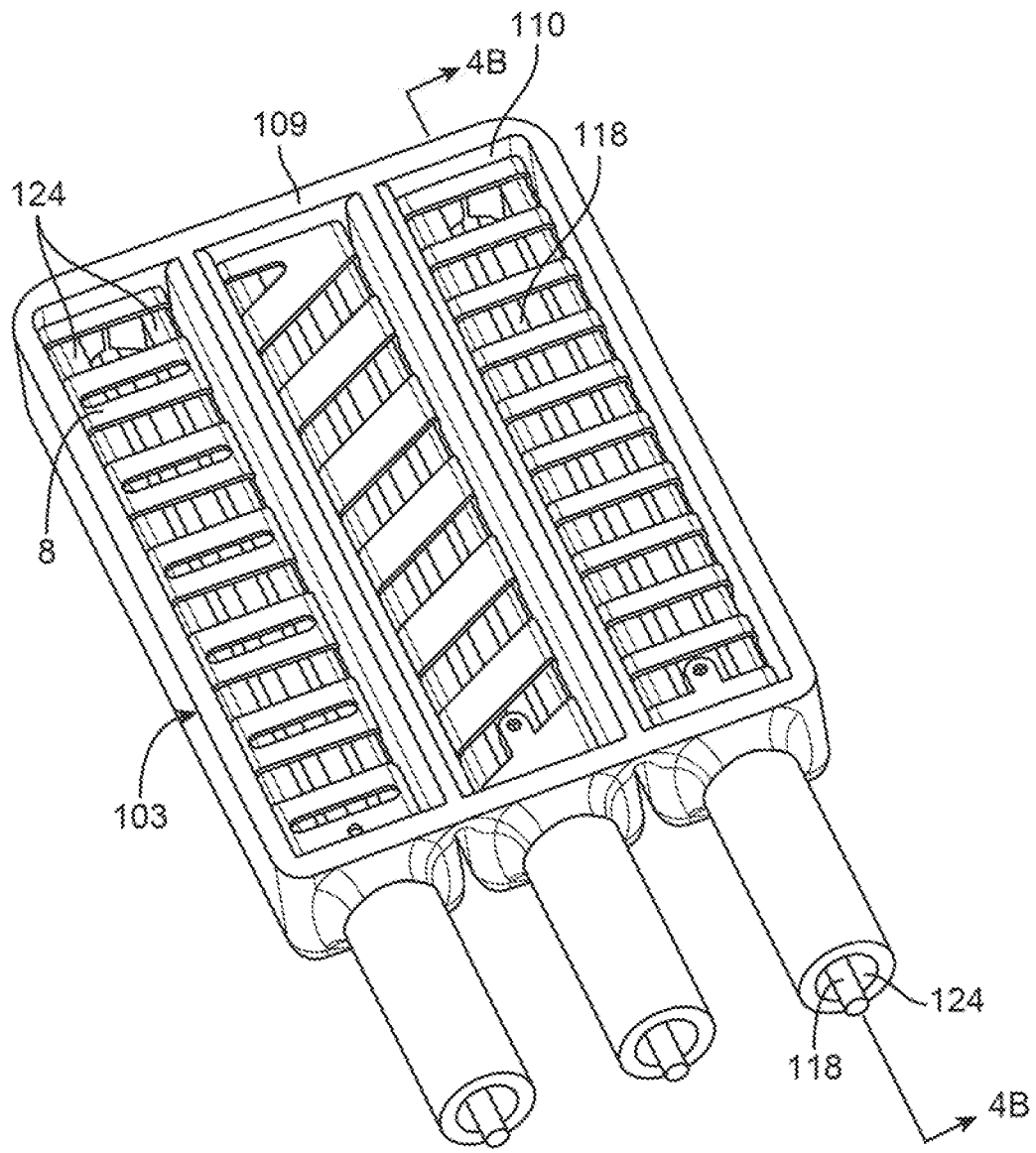
FIG. 4A illustrates an isometric view of a plurality of housing shells to illustrate the fluid delivery supply or lumen having an opening fluidly coupled to the cavity.

FIG. 4A illustrates another isometric, view of a plurality of housing shells 193 to better illustrate the fluid delivery supply or lumen 118 having an opening fluidly coupled to the cavity. In some variations, the opening of the lumen 118 is positioned at a distal end of the cavity 110. As illustrated, the energy transfer elements 8 can be positioned on one or more support surfaces 124 within the cavity. In one construction, the sides of the energy transfer element are positioned between the support surfaces 128 and the side walls of the housing shell where an adhesive, epoxy, or other securing component secures the transfer element within the cavity 110. In the illustrated example, the fluid lumen 118 extends through a vacuum lumen 124 that is in fluid engagement with the cavity 110. Alternatively, the fluid lumen and vacuum lumen can comprise lumens of a multi-lumen tube.

Figure 4B:
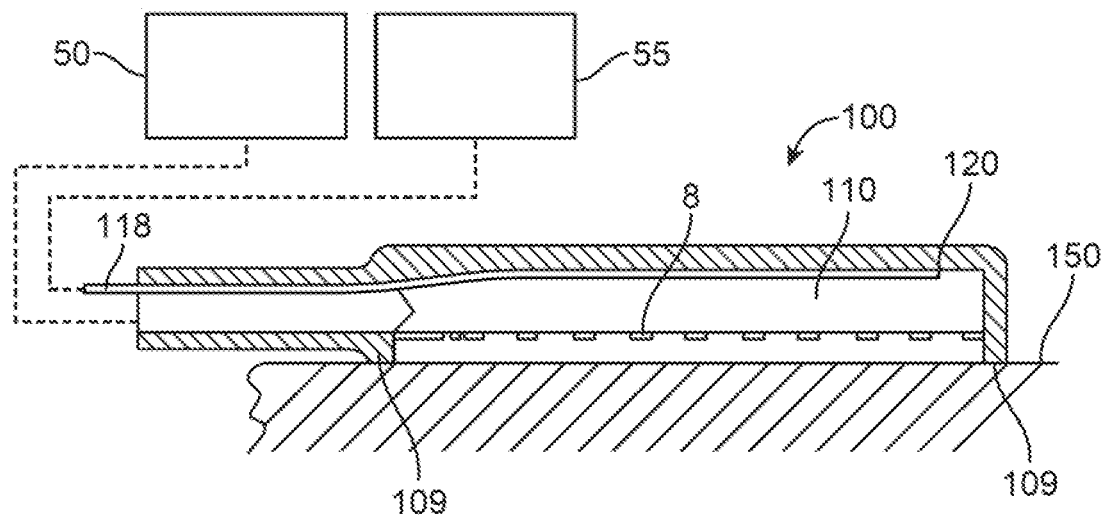
FIG. 4B illustrates a sectional view taken along line 4B-4B of FIG. 4A where the device is further positioned against a tissue surface.
Figure 4C:
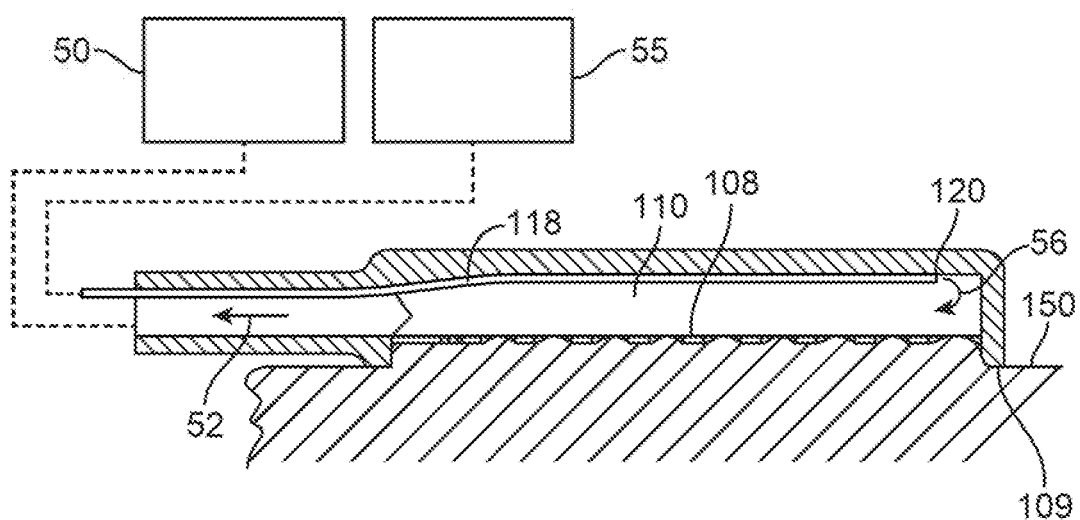
FIG. 4C illustrates the device of FIG. 4B when vacuum is drawn via the vacuum source that is in fluid communication with the cavity using one or more vacuum lumens.

FIG. 4B illustrates a sectional view taken along line 4B-4B of FIG. 4A where the device 100 is further positioned against a tissue surface 150. As shown, the illustrated variation includes energy transfer elements 8 that are recessed within the cavity 110. FIG. 4C illustrates the device of FIG. 4B when vacuum 52 is drawn via the vacuum source 50 that is in fluid communication with the cavity 110 using one or more vacuum lumens. The vacuum 52 causes formation of a seal between the wall of the housing shell 103 and the tissue 150 by drawing tissue into engagement with the wall 108 and also into engagement with the energy transfer element. The wall 109 of the housing shell can be flexible to conform to soft tissue to improve formation of the seal. In those variations where the energy transfer element comprises openings, the tissue 150 can be drawn through the openings. In those cases where a cooling fluid is desired, the formation of the seal also can also cause a drop in pressure in the fluid supply lumen 118 such that fluid 56 is drawn into the cavity 110 at the opening 120 of the fluid supply lumen 118. The fluid 56 is pulled proximally by the vacuum 118 causing flood to pass over the treated tissue and energy transfer element. Next, the physician can apply energy to the energy transfer elements to create the desired tissue treatment pattern. In certain variations of the device, fluid is not used during the procedure. Therefore, those variations of the device can omit a fluid lumen.

Variations of the device 100 can include a plurality of housing shells that each have their own vacuum and/or fluid source. Alternatively, one or more housing shells can share either the vacuum and/or fluid source with other housing shells.

Figure 5A:
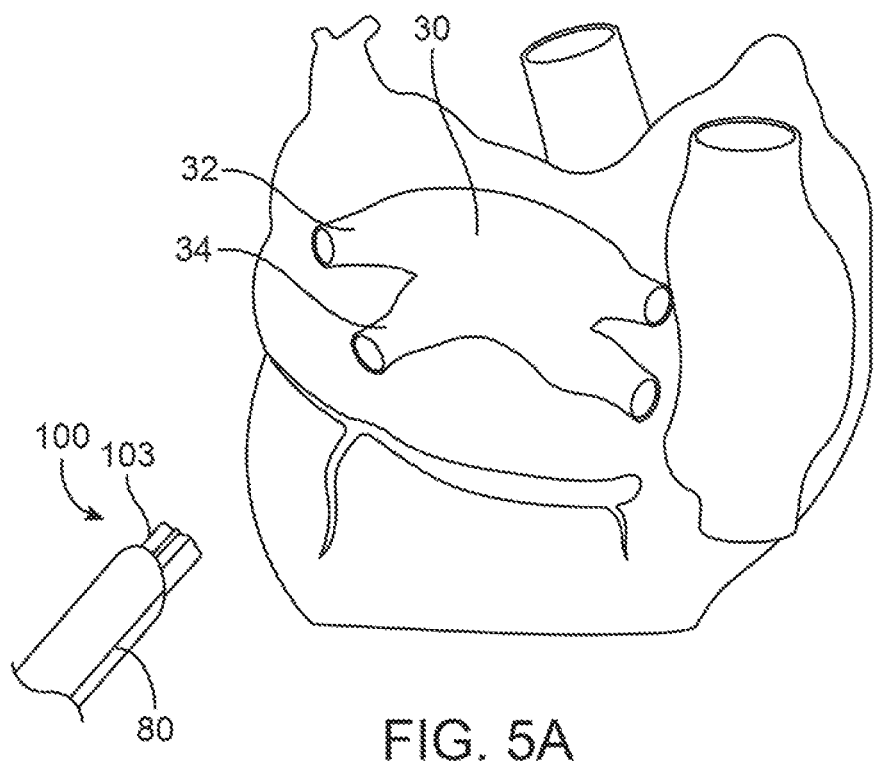
FIGS. 5A to 5C illustrate a method of treating tissue with the devices described herein.
Figure 5B:
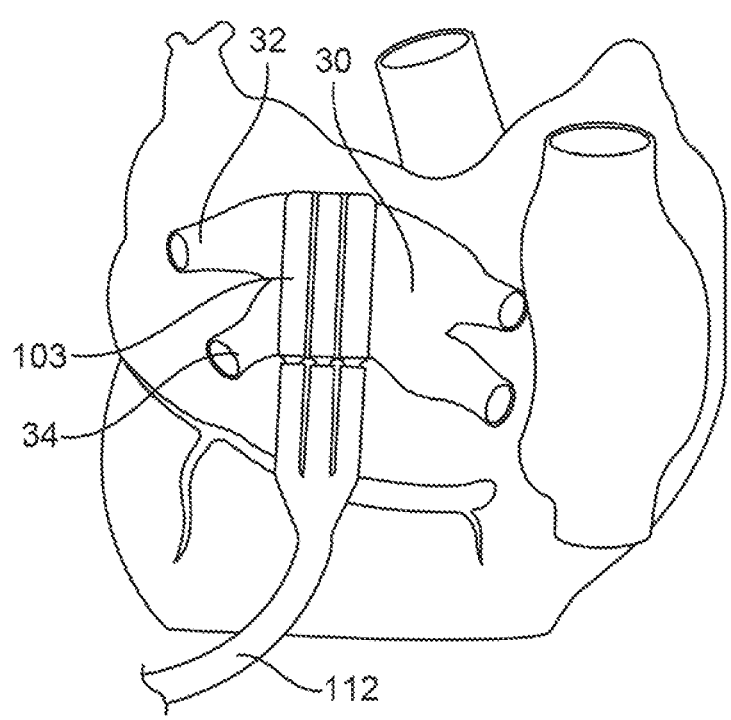
Figure 5C:
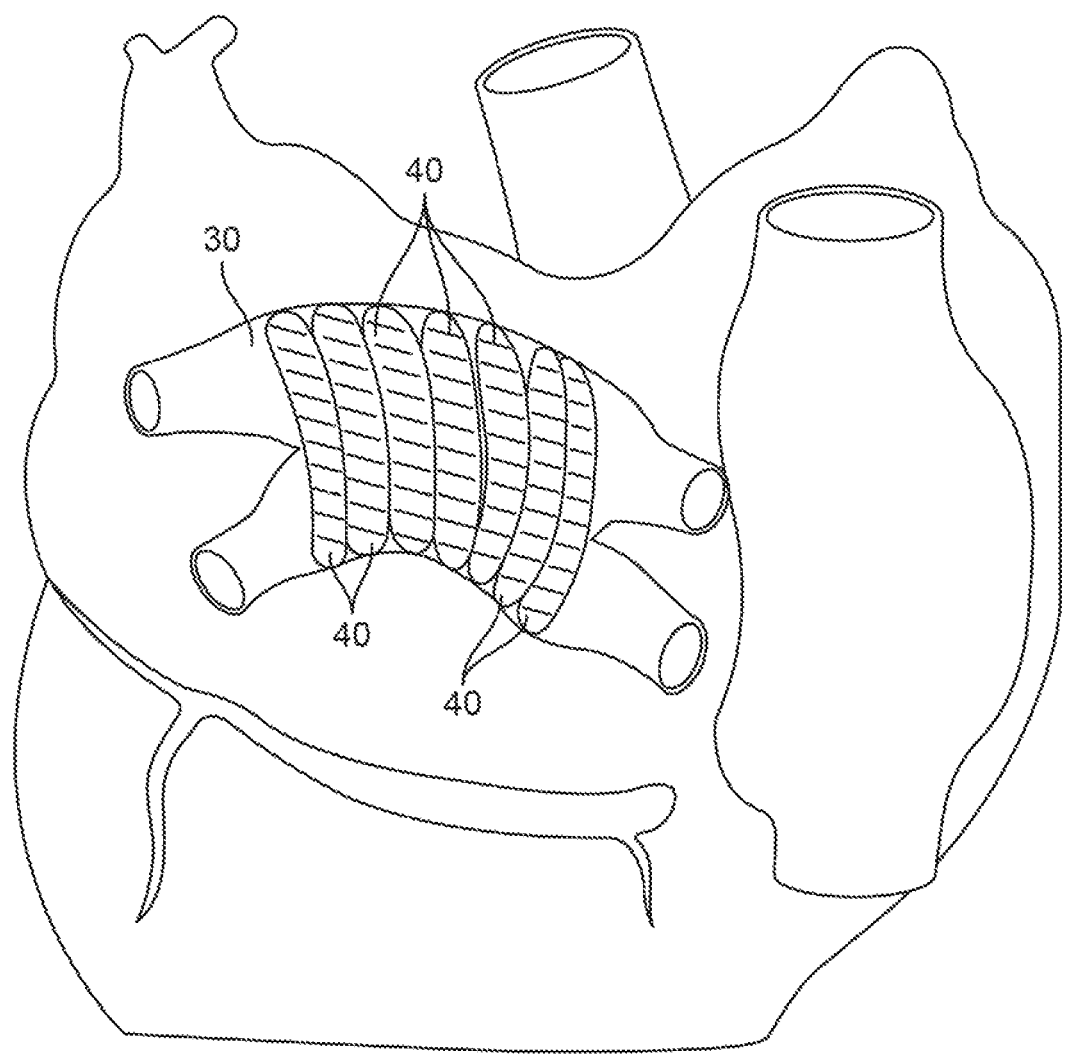

FIGS. 5A to 5C illustrate one method of treating tissue with the devices described herein. For example, as shown in FIG. 5A, a physician can access the body as described above to position a cannula 80 adjacent to a region of tissue. In the illustrated example, the treatment comprises accessing the surface of the left atrium. Therefore, using the cannula 80 to introduce the device 100 allows for a minimized entry incision given that the device is in a compact configuration as discussed above.

Once the device 100 exits a distal opening of the cannula 80, the plurality of housing shells, which were folded along a longitudinal axis unfold as shown in FIG. 5B, assume the deployment configuration which effectively increases a treatment surface of the device by separating the energy transfer elements. As noted above, unfolding of the plurality of housing shells causes the openings of each housing shell to be oriented in parallel and towards the region of tissue.

FIG. 5B illustrates the device where the housing shells 103 are positioned against the left atrium 30 adjacent to the left superior 32 and inferior 34 pulmonary veins. As discussed above, the housing shells are positioned adjacent to the tissue surface such that a vacuum pulled within the cavities of the device cause tissue to form a seal against the opening and secures the housing shells 103 against the left atrium.

Next, energy is applied to each energy transfer element to create a plurality of the elongate treatment patterns in the region of tissue. Energy can either be applied to one energy transfer unit at a time or to more than one energy transfer element. The ability to create side-by-side lesions or treatment regions with the device allows treatment of an increased area of tissue without having to reposition the device. FIG. 5C illustrates treatment of a majority of the left atrium where a number of treatment patterns 40 can be created by only moving the device a few times. Moreover, the device can be repositioned where only one energy transfer element is activated. This prevents multiple treatment of the same region of tissue while ensuring full coverage of the tissue of interest. Any number of permutations are within the scope of this disclosure. For example, the vacuum can be applied to each cavity of the housing shell or to fewer than all cavities. Likewise, application of a vacuum and creation of a treatment pattern can occur simultaneously in each housing shell or can occur sequentially across housing shells and energy transfer elements until the desired pattern is obtained.

Figure 6A:
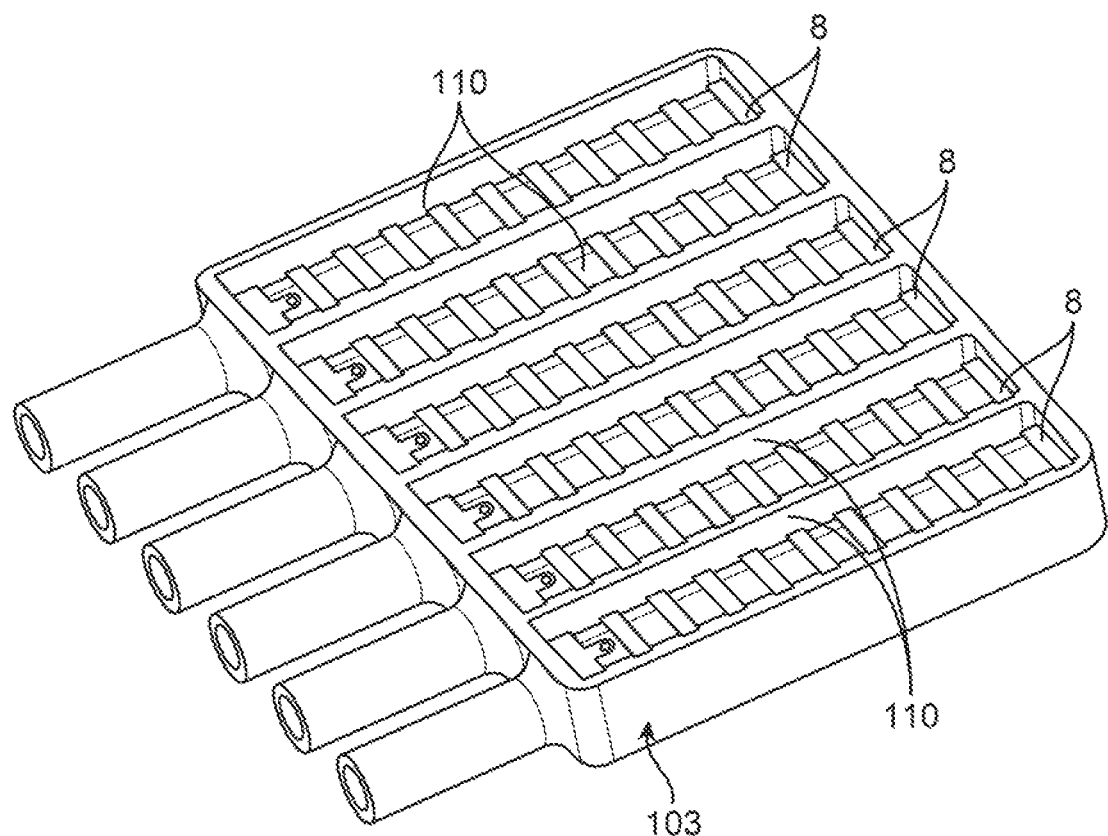
FIG. 6A illustrate another variation of a plurality of housing shells containing energy transfer elements.

FIG. 6A illustrate another variation of a plurality of housing shells 103 containing energy transfer elements 8. As illustrated, variations of the device can include any number of housing shells 103. In the illustrated variation, the device comprises 6 housing shells 103 where each cavity 110 includes a similar energy transfer element.

Figure 6B:
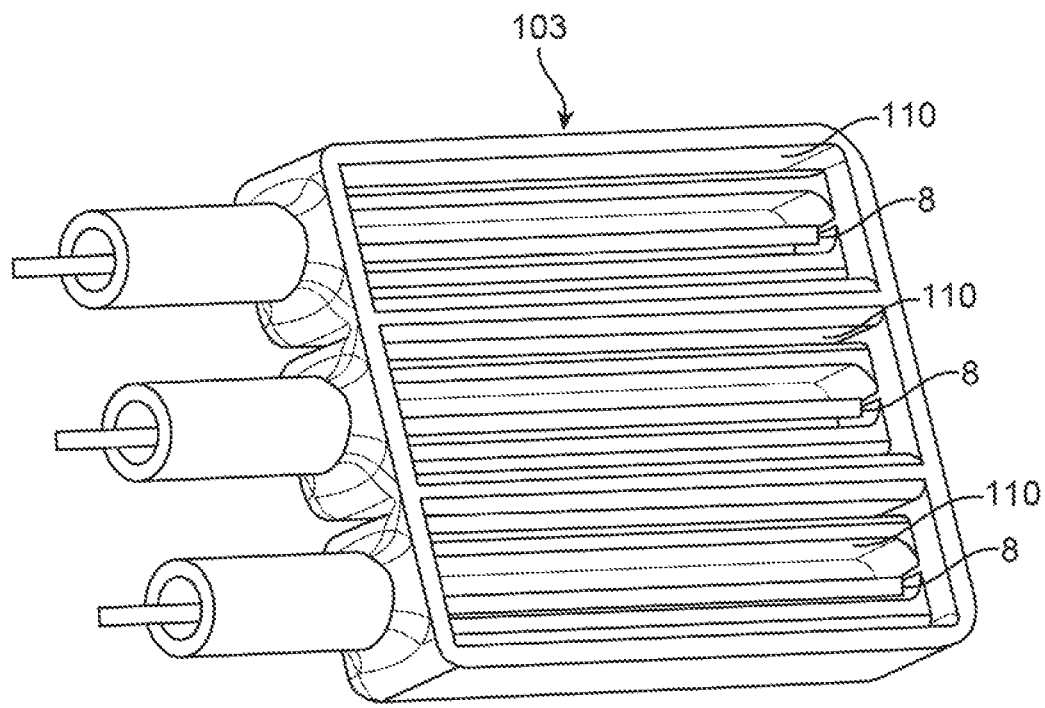
FIG. 6B shows a variation of a plurality of housing shells containing cryogenic probes as the energy transfer elements.

FIG. 6B shows another example of a plurality of housing shells 103 having a cryogenic probe as the energy transfer element 8. Examples of such cryogenic probes are found in commonly assigned U.S. Pat. No. 8,915,908 to Privitera, the entirety of which is incorporated by reference herein.

Figure 7A:
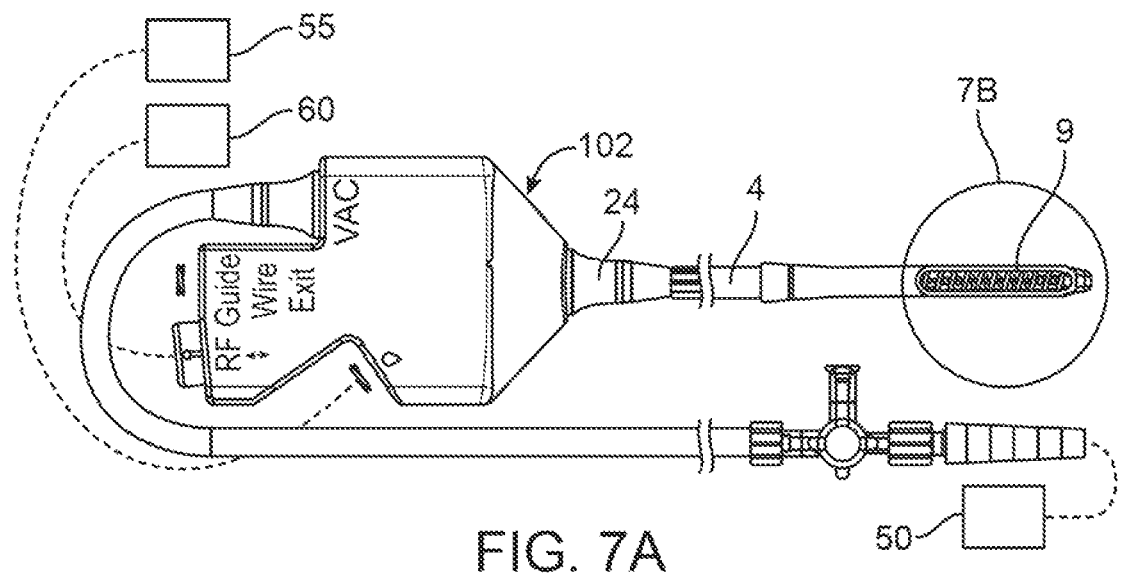
FIGS. 7A to 7C illustrate a variation of treatment device with pacing and/or sensing capabilities as well as an energy transfer element within a single probe.

FIG. 7A illustrates another variation of a device for creating a plurality of side-by-side treatment patterns in tissue. In this variation, a coagulation device consisting of a probe 2 and a handle 102 can be used to create the treatment pattern. The probe 2 again includes a shaft 4 having a housing 9 at a distal section of the shaft 4.

The probe can optionally include sensor to provide pacing and/or sensing. The illustrated probe is intended for exemplary purposes. Any number of devices can be used. For example, the following commonly assigned patents and publication, each of which is incorporated by reference herein, describe coagulation probes that can be used with the positioning system: U.S. Pat. No. 6,893,442 issued May 17, 2005; U.S. Pat. No. 7,063,698 issued Jun. 20, 2006; U.S. Pat. No. 7,410,487 issued Aug. 12, 2008; U.S. Pat. No. 7,572,257 issued Aug. 11, 2009; U.S. Pat. No. 7,758,578 issued Jul. 20, 2010; U.S. Pat. No. 7,780,661 issued Aug. 24, 2010; U.S. Pat. No. 7,803,155 issued Sep. 28, 2010; U.S. Pat. No. 8,034,053 issued Oct. 11, 2011; U.S. Pat. No. 8,235,990 issued Aug. 7, 2012; U.S. Pat. No. 8,241,273 issued Aug. 14, 2012; U.S. Pat. No. 8,454,598 issued Jun. 4, 2013; U.S. Pat. No. 8,465,479 issued Jun. 18, 2013; U.S. Pat. No. 8,858,552 issued Oct. 14, 2014; U.S. Pat. No. 8,888,766 issued Nov. 18, 2014; U.S. Pat. No. 8,998,900 issued Apr. 7, 2015; U.S. Pat. No. 9,308,042 issued Apr. 12, 2016; and US20110282344A1 filed on May 10, 2011.

Figure 7B:
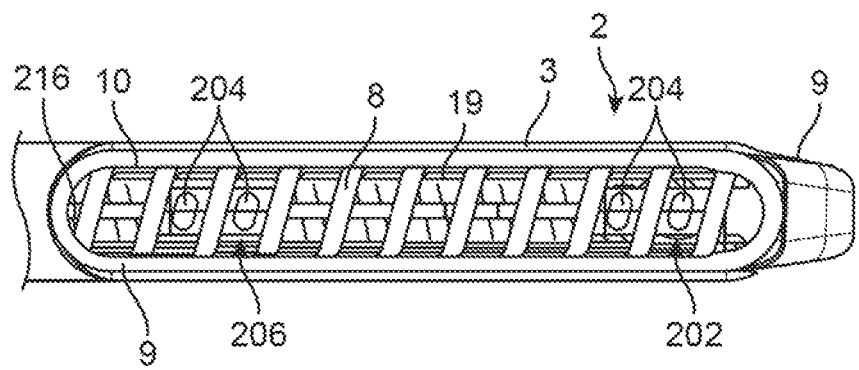

FIG. 7B illustrates a magnified view of the distal end of the probe 2 of FIG. 4A. In this variation, the probe 2 includes a housing 3 having both an energy transfer element 8 and a plurality of diagnostic element assemblies 202 and 206 exposed at the opening 10 of the housing 3. The illustrated variation shows a probe 2 having a coiled energy transfer element 8 with two diagnostic element assemblies 202 and 206. However, additional variations of probes can include a non-helical energy transfer element 8 with any number of diagnostic element assemblies or even a single assembly. As shown, electrodes 204 on the diagnostic element assemblies 202, 206 are positioned between the electrode or element surface (in this case the turns of the coil.) As described herein, the areas between the turns of the coil permit a vacuum force within the housing to secure the opening against tissue and draw the tissue into opening so that tissue contacts the energy transfer element 8 as well as the diagnostic electrodes 204. The housing 3 can also include a flexible lip 9 or extension that assists in securing tissue against the opening 10 to form a vacuum. In some variations of the device it important that the electrodes 204 on the diagnostic assemblies remain electrically isolated from the energy transfer element 8. This can be accomplished by positioning the diagnostic electrodes 204 within the spacing of the element 8 as well as electrically insulating the interior of the element 8. As shown below, the probe 3 can include one or more liners 19 that can support the helical element 8 and/or provide additional insulation to electrically isolate the diagnostic electrodes 204.

Figure 7C:
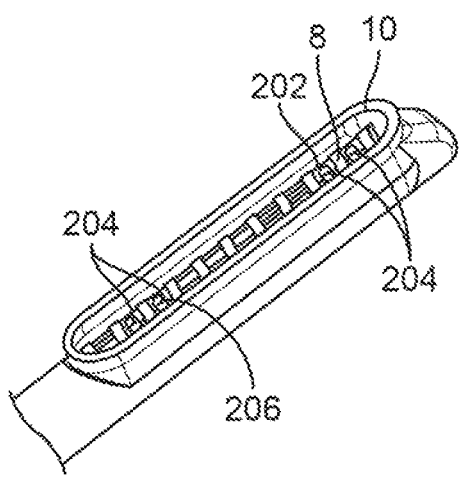

FIG. 7C shows a perspective view of the energy transfer element 8 located within an opening 10 of the probe 2. As shown, the energy transfer element 8 and diagnostic element assemblies 202 and 206 are recessed within the opening 10 so that when the lip 10 forms a seal against tissue the tissue is drawn into the opening 10 and engages the element 8 and electrodes 204 of the diagnostic assemblies 202 and 206.

FIG. 8 shows an example of a positioning system for use with the probe of FIG. 7A. The positioning system 300 comprises a cradle 302 that engages the probe housing (not shown) and is slidably coupled to a guide member 320. The cradle 302 and guide member 320 are coupled to a linkage 332 that is coupled to an actuator assembly 330. In the illustrated example, the actuator assembly comprises a base handle 334 and plunger 336. However, any mechanism can be used that drives and retracts the linkage 332.

Figure 9A:
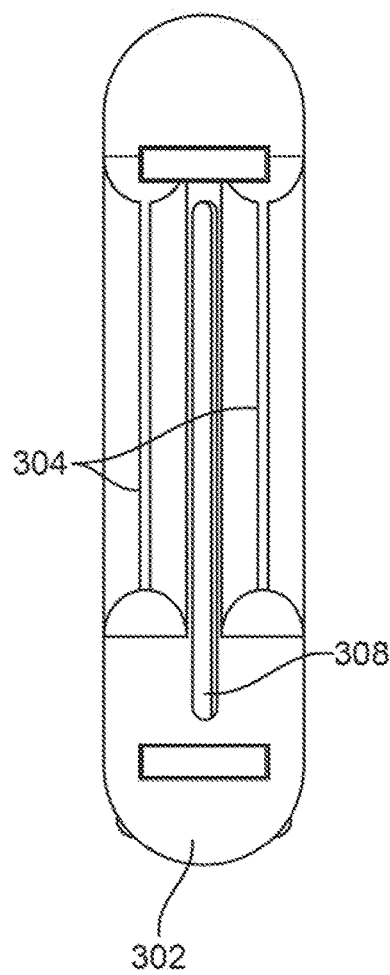
FIGS. 9A, 9B, and 9C show respectively a top view, front view, and side view of a cradle of the positioning system.
Figure 9B:
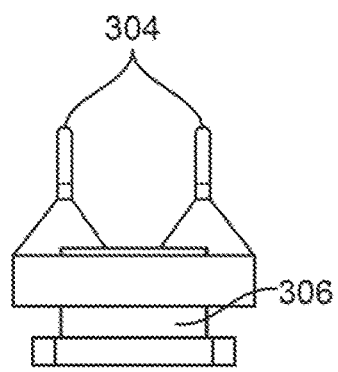
Figure 9C:
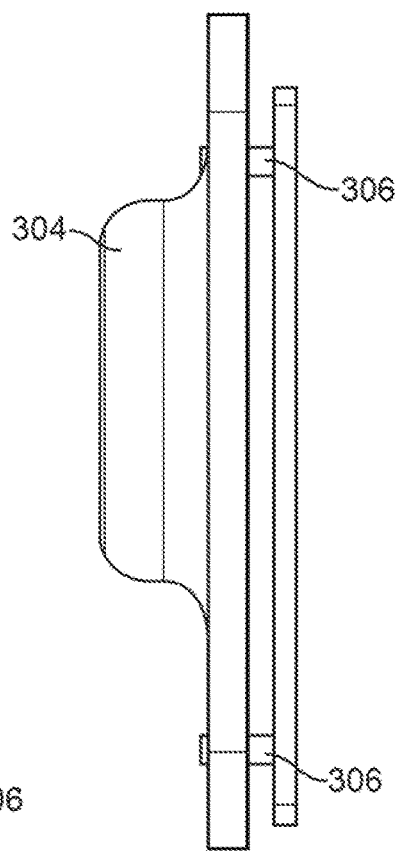
Figure 10A:
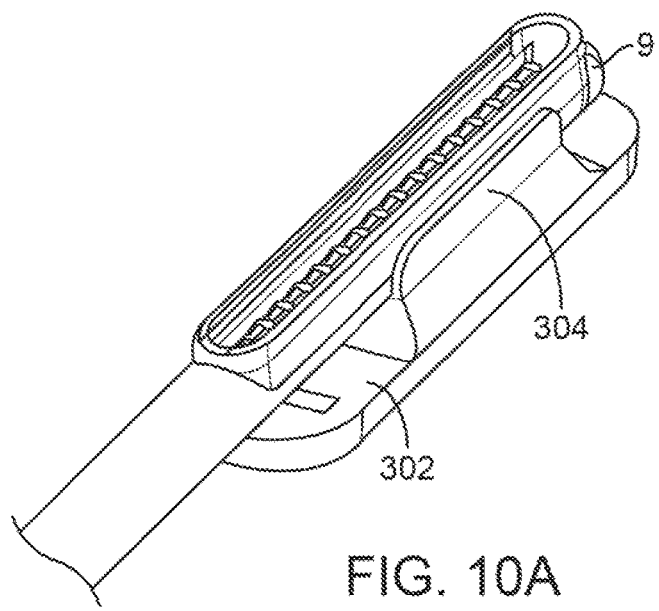
FIG. 10A illustrates a device housing secured within a retaining structure of the cradle.

FIGS. 9A, 9B, and 9C show respectively a top view, front view, and side view of the cradle 302, which includes a retaining structure 304 that secures a housing of the treatment device. The cradle 302 includes rail members 306 that slidably engage with the guide member (not shown). The cradle 302 also includes a slot 308 that allows for moveable engagement with a portion of the linkage (not shown). FIG. 10A illustrates a device housing 9 secured within a retaining structure 304 of the cradle 302. In those variations where the housing 9 is flexible, the retaining structure 304 compresses the housing 9 for retention. Alternatively, or in combination, the cradle 302 can include a clamping structure or openings for securing the housing with a suture or other similar member.

Figure 10B:
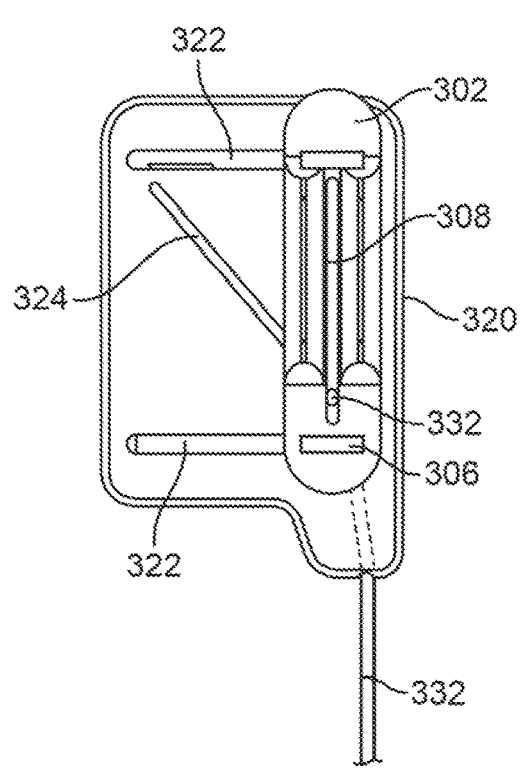
FIGS. 10B and 10C illustrate movement of the cradle across the guide member.
Figure 10C:
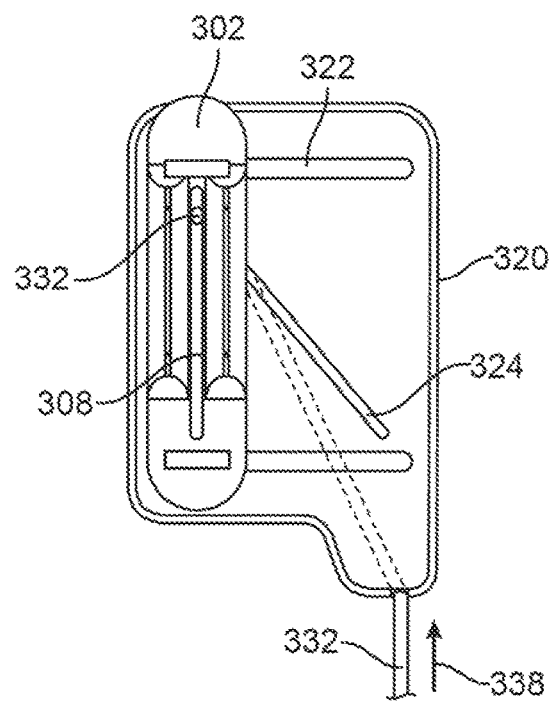

FIGS. 10B and 10C illustrate movement of the cradle 302 across the guide member 320. As illustrated, the guide member 320 can include any number of guide slots 322 that receive the rail members 306 of the cradle 302. The guide member 320 can also include a driving slot 324 through which the linkages 332 couples to the slot 308 in the cradle 302. The linkage 332 is slidably retained in the cradle slot 308 such that movement 338 of the linkage 332 as shown in FIG. 10C causes the linkage 332 to move across the driving slot 324 in the guide member 320 while moving in the cradle slot 308. This movement causes the cradle to move across the guide member 320.

In operation, the guide member 320 can be positioned adjacent to tissue and retained either by use of clamping or similar type device. The treatment device can then be positioned as desired to create a single treatment pattern. Once the pattern is completed, or before the treatment device ceases delivery of vacuum to release from the tissue, the guide member 320 can be secured. Once the guide member is secured, the positioning system can be triggered to move the cradle and device to an adjacent location.

The methods herein may be performed using the subject devices or by other means. The methods may all comprise the act of providing a suitable device. Such provision may be performed by the end user. In other words, the "providing" (e.g., a delivery system) merely requires the end user obtain, access, approach, position, set-up, activate, power-up or otherwise act to provide the requisite device in the subject method. Methods recited herein may be carried out in any order of the recited events which is logically possible, as well as in the recited order of events. In addition, variations of the invention may be used in coagulating other soft tissues such as breast tissue, the liver, the prostate, gastrointestinal tissue, skin, or other soil tissue for the coagulation of cancerous cells; or other collagen based soft tissue for the heat induced shrinking or contraction.

Various exemplary variations of the invention are described herein. Reference is made to these examples in a non-limiting sense. They are provided to illustrate more broadly applicable aspects of the present invention. Various changes may be made to the invention described and equivalents may be substituted without departing from the true spirit and scope of the invention, in addition, many modifications may be made to adapt a particular situation, material, composition of matter, process, process act(s) or step(s) to the objective(s), spirit or scope of the present invention. All such modifications are intended to be within the scope of the claims made herein. Exemplary aspects of the invention, together with details regarding material selection and manufacture have been set forth above. As for other details of the present invention, these may be appreciated in connection with the above-referenced patents and publications as well as generally know or appreciated by those with skill in the art.

The same may hold true with respect to method-based aspects of the invention in terms of additional acts as commonly or logically employed. In addition, though the invention has been described in reference to several examples, optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in the appended claims, the singular forms "a," "an," "said," and "the" include plural referents unless the specifically stated otherwise. In other words, use of these articles allow for "at least one" of the subject item in the description above as well as the claims below. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in the claims shall allow for the inclusion of any additional element—irrespective of whether a given number of elements are enumerated in the claim, or the addition of a feature could be regarded as transforming the nature of an element set forth in the claims.

What is claimed is:

1. A method of treating tissue, the method comprising:
    positioning a cannula adjacent to a region of tissue;
    advancing a medical device through a distal opening of the cannula, where the medical device includes a plurality of housing shells folded along a longitudinal axis of the plurality of housing shells and each of the plurality of housing shells are in direct contact with an adjacent housing shell along a longitudinal edge of the housing shell where the longitudinal edge is parallel to the longitudinal axis, where each of the plurality of housing shells comprises an opening that exposes an energy transfer element located within a cavity of each of the housing shells, where a length of each energy transfer element is greater than a width such that the energy transfer element is configured to create an elongate treatment pattern;
    unfolding the plurality of housing shells such that the openings of each housing shell are oriented in parallel and towards the region of tissue;
    contacting the plurality of housing shells against a surface of tissue such that each energy transfer element is positioned adjacent to tissue; and
    applying energy to each energy transfer element to create a plurality of the elongate treatment patterns in the region of tissue.

2. The method of claim 1, further comprising applying a vacuum through at least one cavity of the plurality of housing shells to secure the at least one housing shell against the region of tissue.

3. The method of claim 2, where applying the vacuum through the at least one cavity of the plurality of housing shells comprising applying the vacuum through each cavity of each of the plurality of housing shells.

4. The method of claim 2, where applying the vacuum through the at least one cavity of the plurality of housing shells further draws a portion of the region of tissue to contact the energy transfer element.

5. The method of claim 4, where at least one energy transfer element comprises an opening, where applying the vacuum through the at least one cavity causes the region of tissue to be pulled into the opening of the at least one energy transfer element.

6. The method of claim 2, further comprising delivering a fluid through the at least one cavity of the plurality of housing shells.

7. The method of claim 6, where applying the vacuum through the at least one cavity causes the tissue region to form a seal against the opening in the at least one of the plurality of housing shells, where the seal causes fluid to flow through the at least one cavity.

8. The method of claim 7, where delivering the fluid through the at least one cavity of the plurality of housing shells comprises causing the vacuum to draw the fluid through the at least one cavity.

9. The method of claim 6, where delivering the fluid comprises fluidly coupling each cavity of the plurality of housing shells to at least one fluid supply.

10. The method of claim 9, where fluidly coupling each cavity of the plurality of housing shells comprises fluidly coupling each cavity to one of a plurality of fluid supplies.

11. The method of claim 1, where the region of tissue comprises a left atrium of the heart.

12. The method of claim 1, wherein the medical device comprises a manifold, wherein the manifold is coupled to the plurality of housing shells.

13. The method of claim 12, wherein at least part of the manifold and the plurality of housing shells are flattened when the plurality of housing shells are unfolded.

* * * * *